US009149494B2

(12) United States Patent
Sagi et al.

(10) Patent No.: US 9,149,494 B2
(45) Date of Patent: Oct. 6, 2015

(54) ORALLY-ADMINISTRABLE COMPOSITIONS COMPRISING STABLE AMORPHOUS CALCIUM CARBONATE

(75) Inventors: Amir Sagi, Omer (IL); Amir Berman, Omer (IL); Yosef Ben, D.N. Arava (IL)

(73) Assignee: BEN-GURION UNIVERSITY OF THE NEGEV RESEARCH AND DEVELOPMENT AUTHORITY, Beer-Sheva (IL)

(*) Notice: Subject to any disclaimer, the term of this patent is extended or adjusted under 35 U.S.C. 154(b) by 1230 days.

(21) Appl. No.: 11/604,006

(22) Filed: Nov. 24, 2006

(65) Prior Publication Data

US 2008/0199540 A1 Aug. 21, 2008

Related U.S. Application Data

(63) Continuation-in-part of application No. PCT/IL2005/000545, filed on May 26, 2005.

(60) Provisional application No. 60/574,208, filed on May 26, 2004.

(51) Int. Cl.
*A61K 33/10* (2006.01)

(52) U.S. Cl.
CPC ....................................... *A61K 33/10* (2013.01)

(58) Field of Classification Search
CPC ....................................................... A61K 33/10
See application file for complete search history.

(56) References Cited

U.S. PATENT DOCUMENTS

| | | | |
|---|---|---|---|
| 4,199,496 A | 4/1980 | Peniston et al. | |
| 4,237,147 A * | 12/1980 | Merten et al. | 426/590 |
| 4,964,894 A * | 10/1990 | Freepons | 504/292 |
| 6,569,472 B1 | 5/2003 | Zyck et al. | |

FOREIGN PATENT DOCUMENTS

| | | | |
|---|---|---|---|
| EP | 0 052 677 | | 6/1982 |
| EP | 0052677 A1 * | | 6/1982 |
| JP | 09009871 A * | | 1/1997 |
| JP | H10-236957 | | 9/1998 |
| KR | 10-2002-0082813 | | 10/2002 |

OTHER PUBLICATIONS

Raz et al., "Stable Amorphous Calcium Carbonate Is the Main Component of the Calcium Storage Structures of the Crustacean *Orchestia cavimana*", Dec. 2002, Bio. Bull., vol. 203, pp. 269-274.*
Travis, Structural Features of Mineralization From Tissue to Macromolecular Levels of Organization in the Decapod Crustacea, May 1963, Annals of the New York Academy of Sciences, vol. 109, pp. 174-245.*
Takagi et al., Immunolocalization of Gastrolith Matrix Protein (GAMP) in the Gastroliths and Exoskeleton of Crayfish, *Procambarus clarkii*, 2000, Zoological Sciences, vol. 17, pp. 179-184.*
Ishii et al. Solubilization and Chemical Characterization of an Insoluble Matrix Protein in the Gastrolith of Crayfish, *Procambarus clarkii*, 1998, Biosci. Biotechnol. Biochem. vol. 62 iss. 2, pp. 291-296.*
Travis, The Deposition of Skeletal Structures in the Crustacea. I. The Histology of the Gastrolith Skeletal Tissue Complex and the Gastrolith in the Crayfish, Orconecetes (Cambarus) Virilis Hagen—Decapoda, Feb. 1, 1960, The Biological Bulletin, vol. 118 No. 1, pp. 137-149.*
Ishii et al., "Solubilization and Chemical Characterization of an Insoluble Matrix Protein in the Gastroliths of a Crayfish, *Procambarus clarkii*", Biosci. Biotechnol. Biochem., vol. 62, 4 pages, 1998.
Addadi et al., "Amorphous Calium Carbonate and Its Roles in Biomineralization", Advanced Materials, vol. 15, No. 12, pp. 966-970, Jun. 17, 2003.
Withnall, "Biology of Yabbies (cherax destructor)", Aquaculture Information Notes, Department of Primary Industries, 6 pages, Jun. 2000.
Raz et al., "Stable Amorphous Calcium Carbonate is the Main Component of the Calcium Storage Structures of the Crustacean *Orchestia cavimana*", Biol. Bull. vol. 203, pp. 269-274, Dec. 2002.
Parnes & Sagi "Intensification of redclaw crayfish *Cherax quadricarinatus* culture I. Hatchery and nursery system" Aquacultural Engineering 26: 251-262 (2002).
Manor et al. "Intensification of redclaw crayfish *Cherax quadricarinatus* culture II. Growout in a separate cell system" Aquacultural Engineering 26: 263-276 (2002).
Hu et al. "Effect of calcium supplements on osteoporosis by using nuclear analytical techniques" J. Radioanalytical & Nuclear Chemistry 259: 369-373 (Mar. 2004).
Shian et al. "Effect of commercial fortified calcium products on calcium status in rats" Acta Nutrimenta Sinica 1997-03-018 (Sep. 1997).
K. Akamatsu, "Oriental Drugs, New Revision," 1st Ed. Ishiyaku Shuppan K.K., Apr. 20, 1970, p. 911.
M. Ito, Notice of Reasons for Rejection in counterpart foreign application JP 2007-514322, mailed Aug. 16, 2011, seven pages, explaining the relevance of the above non-English language documents.
Huxley "The natural history of the common crayfish" in the Crayfish: An Introduction to the Study of Zoology, Chapter 1, pp. 1-45 and reprinted as 20 HTML sheets (1879).
J.D. "Oculi cancrorum: Very proper for falls and a pleurisy" Annals of the Royal College of Surgeons of England, 20: 57-58 (Jan. 1957).

(Continued)

*Primary Examiner* — Ali Soroush
(74) *Attorney, Agent, or Firm* — Rothwell, Figg, Ernst & Manbeck, P.C.

(57) ABSTRACT

The present invention provides orally-administrable compositions comprising stable amorphous calcium carbonate (ACC). The compositions are preferably prepared as solid dosage forms such as tablets, capsules and powders. The present invention further provides methods for supplementing oral calcium intake in subjects and as well as methods for treating osteoporosis, osteomalacia and related diseases.

20 Claims, 5 Drawing Sheets

(56) References Cited

OTHER PUBLICATIONS

Komuro "Treatment manual for renal diseases VIII. 313. Calcium preparations" Kidney and Dialysis Special Edition 41:871-872 (1996).

Nagasawa & Ishii "The chemical structure of insoluble organic matrix contained in *Procambarus clarkii* gastrolith" Kaiyo Monthly 28:688-693 (1996).

Ito, partial English translation of Office Action for counterpart Japanese application, Serial No. 2007-514322, two pages, mailed Feb. 28, 2012.

Addadi et al., (2003) Taking Advantage of Disorder: Amorphous Calcium Carbonate and Its Roles in Biomineralization. Advanced Materials 15(12): 959-970.

Universal Filters, Inc. "Mesh to Micron Conversion Chart" at http://www.universalfilters.com/MMCC.html, two pages (2008-2011).

* cited by examiner

ORALLY-ADMINISTRABLE COMPOSITIONS COMPRISING STABLE AMORPHOUS CALCIUM CARBONATE

This application is a continuation-in-part of Application No. PCT/IL2005/000545, filed 25 May 2005, which claims priority over U.S. provisional application Ser. No. 60/574,208, filed 26 May 2004.

Calcium is the most abundant mineral in the human body, comprising over 1.5% of the total body weight. Recent research indicated that modern diets contain only around one-third of the calcium needed. The food additive market is very large and fast growing, out of which calcium additives occupy a significant niche. Calcium supplements, primarily for prophylactic treatment of osteoporosis, are generally prepared using calcium carbonate from terrestrial deposits or from marine origin such as corals or seashells (along with organic calcium salts, in which the calcium content is lower). Both corals and seashell sources are crystalline. It is claimed in several nutritional studies that the bio-availability of calcium from these crystalline forms of calcium carbonate is low, especially in the elderly, when the stomach acid production is reduced. A need therefore exists for an alternative calcium source for use in the preparation of food additives and therapeutic compositions.

To this end, amorphous calcium carbonate (ACC), with its higher solubility than crystalline calcium carbonate minerals (e.g. calcite and aragonite), would appear to provide a preferable alternative for calcium consumption over the existing crystalline calcium carbonates used in prior art formulations.

However, the industrial-scale preparation and/or purification of amorphous mineral deposits (such as ACC) is problematic, in view of the rarity of such deposits in nature, which may in part be due to their inherent instability and the consequent need for specialized compounds in order to prevent spontaneous transformation into the more stable crystalline mineral.

It is established that in certain crustaceans, such as the crayfish, *Cherax quadricarinatus*, other crayfish species, and other decapod crustacean, ACC is the main mineral used for the hardening of the exoskeleton, where it is deposited in preformed organic matrix composed of chitin compartments and proteins. The crayfish life-cycle involves periodic molting, during which the amorphous mineral is resorbed from the exoskeleton, mobilized and temporarily stored in a dedicated organ, the gastrolith. Following molting, gastroliths are rapidly dissolved in the stomach by acid digestion, and the dissolved mineral is recycled and redeposited in the new exoskeleton.

The present invention is therefore primarily directed to orally-administrable compositions comprising stable ACC. The descriptor "stable" is used herein to indicate that the amorphous calcium carbonate is present in association with organic material, the role of which is to maintain said calcium carbonate in an amorphous state for long periods of time (e.g. from several months to several years) without any substantial conversion to crystalline forms. The term "orally-administrable compositions" as used herein includes both pharmaceutical and nutraceutical compositions, as well as food supplements within its scope.

In one embodiment of the present invention, the stable ACC present in the composition displays a FTIR spectrum having a broad absorption band centered at 1500 $cm^{-1}$ and a peak at 870 $cm^{-1}$, both of which are indicative of ACC, and a peak at 1650 $cm^{-1}$, indicative of chitin. Typically, the FTIR spectrum obtained from the stable ACC used in the presently-disclosed compositions is similar to that shown in FIG. 2.

In another embodiment, the stable ACC present in the composition displays an X-ray diffraction pattern displaying broad peaks centered at approximately $2\theta=30°$ and at approximately $2\theta=45°$, indicative of ACC and a peak at approximately $2\theta=19°$, indicative of chitin, said pattern being essentially free of a signal indicative of crystalline calcium carbonate. In the present context, the term "essentially free of a signal indicative of crystalline calcium carbonate" should be taken to mean that if such a signal is at all detectable, it is produced by crystalline calcium carbonate present in an amount that constitutes no more than 5% (w/w) of the total calcium carbonate content. Typically, however, the crystalline calcium carbonate content is no more than 1%, while preferably, no crystalline calcium carbonate is present.

Typically, the X-ray diffraction spectrum obtained from the stable ACC used in the presently-disclosed compositions is similar to that shown in FIG. 1.

The orally-administrable compositions of the present invention may also be characterized in terms of the proteins found in the organic matrix associated with the ACC. In one preferred embodiment, the organic matrix associated with the ACC comprises chitin and proteins having molecular weights of approximately 218, 184, 138, 129, 71, 66, 55, 51, 43, 30, 25, 17 kDa, as determined by SDS-PAGE analysis. Typically, the stable ACC is characterized by having an SDS-PAGE electrophoretic profile similar to that shown in FIG. 5.

In one particularly preferred embodiment of the invention, the aforementioned orally-administrable composition comprises calcified material obtained from any decapod crustacean including the crayfish group, and particularly, crustaceans of the *Cherax* genus. In a particularly preferred embodiment, the calcified material is obtained from the crayfish *C. quadricarinatus*. The most preferred anatomical source for the aforementioned calcified material is the gastrolith organ. Alternatively, the calcified material may be obtained from the exoskeleton of the crustacean, preferably from the discarded exoskeleton following molting (exuvia). The crustacean-derived calcified material may be present in the compositions of the present invention in any physical form suitable for administration to human and animal subjects in need thereof. In one embodiment, the gastroliths or exoskeletal material may be very simply prepared by means of cleaning said material in the physical form in which it was harvested (e.g. intact gastroliths, or large fragments thereof). More typically, however, the calcified material will be prepared by grinding the gastrolith or exoskeleton pieces to a powder.

Preferably, the orally-administrable composition of the present invention is prepared as a solid dosage form. Thus, in the case of ground gastrolith or exoskeleton-derived powder may be used to load capsules or be compressed or otherwise formed into tablets. Other suitable solid dosage forms include powders, granulates, sachets, lozenges and pastilles. While, in the case of some of the aforementioned solid dosage forms, the ACC and the associated organic matrix constitute the bulk of the material (along with minor inorganic components), said dosage forms will normally further comprise one or more excipients, as well known in the art. Examples of excipients include (but are not limited to) diluents (e.g. microcrystalline cellulose, pregelatinized starch), binders (e.g. carbopol, povidone, xanthan gum), fillers (e.g. lactose), lubricants (e.g. magnesium stearate, stearic acid, sodium stearyl fumarate), glidants (e.g. talc, colloidal silicon dioxide) and disintegrants (e.g. alginic acid, carboxymethylcellulose, carboxymethyl starch, croscarmellose sodium, sodium starch glycolate). It is also to be noted that the organic matrix of the stable ACC may, in certain circumstances, also function as an intrinsic binder.

Solid dosage forms in the forms of tablets or caplets may be manufactured by a variety of different methods, as are well known in the art, included direct compression using a tablet punch. As an alternative to direct compression, the active ingredient and excipients may be combined by dry blending, and then subjected to dry granulation prior to tablet compression. A further alternative method is to utilize wet granulation, in which at least some of the excipients, together with the active ingredient, are blended and then further mixed in the presence of a granulation liquid. Following aggregation of the various powders, the aggregates (i.e. granules) are then sized by screening or milling and dried.

Solid formulation blends for loading into capsules (such as soft gelatin capsules) may be prepared by dry blending, or by wet or dry granulation prior to being introduced into said capsules.

In further preferred embodiments, the calcified material may also be prepared in the form of an orally-administrable liquid suspension or gel. In the case of liquid suspensions, in addition to the active ingredients (i.e. the ACC and its associated organic matrix constituents), the formulation may also contain a variety of other liquid or solid excipients, including (but not limited to) emulsifying agents (e.g. carbomer, cetyl alcohol, gelatin), solvents (e.g. water, vegetable oil, glycerin), flavoring agents (e.g. vanillin, fruit acids, menthol), sweeteners (e.g. sucrose, fructose, aspartame, saccharin) and buffers.

Further information relating to the preparation of solid, liquid and gel dosage forms that are suitable for use in the present invention may be obtained from any standard pharmaceutical reference work, such as Remington's Pharmaceutical Science (Martin E W [1995], Mack Publishing Company, 19th ed.).

The orally-administrable compositions comprising stable amorphous calcium carbonate disclosed hereinabove and described in more detail hereinbelow, may be used as food additives or supplements, in order to increase the amount of dietary calcium ingested by a human or animal subject in regular foodstuffs. In another embodiment, the compositions of the present invention may also be used therapeutically, in the management of medical conditions associated with subnormal levels of blood, tissue or skeletal calcium, or which otherwise may be improved by the administration of calcium. Such conditions include, but are not limited to: osteoporosis, bone repair following injury, osteomalacia and hypocalcemia.

In another aspect, the present invention is also directed to a method for optimizing the harvesting of crayfish gastroliths, wherein said method comprises the steps of:
 a) selecting crayfish having weights within a pre-determined range;
 b) monitoring gastrolith development using digital X-ray image analysis;
 c) optionally inducing gastrolith formation by physiological and endocrinological;
 d) calculating a Molting Mineralization Index (MMI) for each crayfish, wherein the MMI is the ratio of gastrolith width to carapace length; and
 e) selecting for harvest those crayfish having an MMI greater than a pre-determined value, indicating that the crustacean is nearing its molt (approx 2 days) and the gastrolith has reached its maximal calcium content.

The optional stage of gastrolith formation induction, mentioned hereinabove, may comprise various procedures well known in the art such as manipulating the X organ sinus gland complex and/or controlling the level of ecdysteroids.

In the case of *C. quadricarinatus*, the pre-determined weight range in step (a) is 25-80 g, and the pre-determined MMI value is 0.1.

In another embodiment of the above-defined method for optimizing the harvesting of crayfish gastroliths, said method comprises the steps of:
 a) selecting crayfish having weights within a pre-determined range;
 b) monitoring gastrolith development using digital X-ray imaging;
 c) optionally inducing gastrolith formation by physiological and endocrinological means;
 d) obtaining a background-corrected digital image from the raw X-ray image obtained in step (b) and estimating therefrom the number of days remaining until optimal gastrolith development;
 e) classifying the crayfish according to their stage of gastrolith development, on the basis of the time estimate produced in step (d); and
 f) selecting for harvest those crayfish classified in step (e) as having optimally-developed gastroliths.

In yet another aspect, the present invention is directed to a process for preparing an orally-administrable composition comprising stable amorphous calcium carbonate, wherein said process comprises the steps of harvesting gastroliths from crayfish, grinding said gastroliths to a powder, and using said powder to prepare an orally-administered dosage form. In one preferred embodiment of this aspect of the invention, the gastrolith harvesting step is performed using digital X-ray analysis as described hereinabove.

The present invention further encompasses a method for supplementing oral calcium intake in subjects of need of such supplementation, wherein said method comprises the oral administration of a composition comprising stable ACC from crustacean origin or alternatively synthetically produced with specific matrix components to stabilize the otherwise metastable mineral. Such supplementation may be of benefit as part of a preventive regime, for example in order to prevent the onset of osteoporosis or similar diseases.

The present invention also provides a method for treating a disease selected from the group consisting of osteoporosis, bone repair following injuries, osteomalacia, hypocalcemia and other bone diseases, wherein said method comprises the oral administration of a composition comprising a therapeutically-effective amount of stable ACC. A "therapeutically-effective amount" according to the present invention may be defined as any amount of stable ACC that is judged by the prescribing physician or other health care professional to be sufficient to produce the desired therapeutic effect, either as a single dose, or when repeated in a multiple-dose regime. Typical daily dose for an adult may vary in the range of 0.5 to 3 g, while typical daily dose for a child may vary within the range of 0.1 to 1 g.

All the above and other characteristics and advantages of the present invention will be further understood from the following illustrative and non-limitative examples of preferred embodiments thereof, and from the accompanying drawings.

The following examples are provided for illustrative purposes and in order to more particularly explain and describe the present invention. The present invention, however, is not limited to the particular embodiments disclosed in these examples.

EXAMPLE 1

Chemical Analysis of the Crayfish Gastrolith

When their gastroliths reach their maximal size, near molting time, the animals (of the crayfish species *Cherax quadricarinatus*) were dissected and the gastroliths harvested. The gastroliths were then washed in water, air-dried and stored in a refrigerator until further use. 10 g of the washed and dried crayfish gastrolith were then prepared for total chemical analysis.

The chemical analysis was performed using the following methods: The analyses were performed using Inductively Coupled Plasma (ICP) flame photometry and UV spectrometry. Moisture content was determined by baking to 200 deg C. Carbonate was determined by the sample weight loss upon baking to 900 deg C. due to release of carbon dioxide.

The results of the chemical analyses are shown in the following table:

| The analyte | Weight percentage |
| --- | --- |
| Calcium carbonate ($CaCO_3$) | 57.5 |
| Carbonate (not bounded to Ca) | 7 |
| Moisture | 13 |
| Organic (biologic) matter | 11 |
| Phosphorus ($P^{-3}$) | (2.2) |
| As orthophosphate ($P_2O_5$) | 5.3 |
| Magnesium ($Mg^{+2}$) | 0.7 |
| Sodium ($Na^{+1}$) | 2.3 |
| Chlorine ($Cl^{-1}$) | 0.01 |
| Sulfur ($S^{-2}$) | <0.01 |
| Fluorine ($F^{-1}$) | n.d. |
| Potassium ($K^{+1}$) | 1.9 |
| Strontium ($Sr^{+2}$) | 1.28 |
| Total | 100 |

EXAMPLE 2

Further Analysis of the Crayfish Gastrolith

Figure 1:
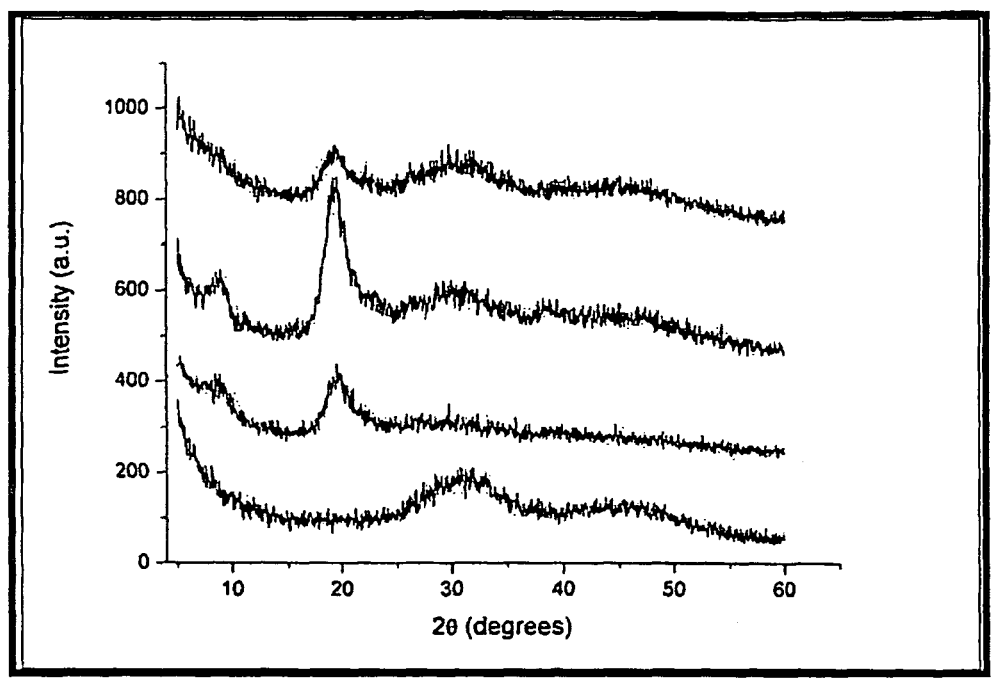
FIG. 1 depicts the results of an x-ray diffraction analysis of crayfish gastrolith and cuticle, taken at various molt stages.

The composition of the gastroliths and cuticles in the crayfish (*C. quadricarinatus*; prepared as described in Example 1) was further characterized using a Philips 1050/70 X-ray powder diffractometer with copper K$\alpha$ line ($\lambda$=1.54 Å). The results of a typical analysis are shown in FIG. 1. Four separate diffractograms are shown on a single pair of axes. The upper three lines correspond with samples of cuticle taken (from above to below) at the intermolt, premolt and postmolt stages. The lowest line corresponds with a gastrolith sample. The most notable feature of these diffractograms is the absence of any signal that could be attributed to crystalline calcium carbonate. The broad peaks located at approximately $2\theta=30°$ and at approximately $2\theta=45°$ are due to ACC, while the peak located at $2\theta=19°$ is attributed to chitin.

Figure 2:
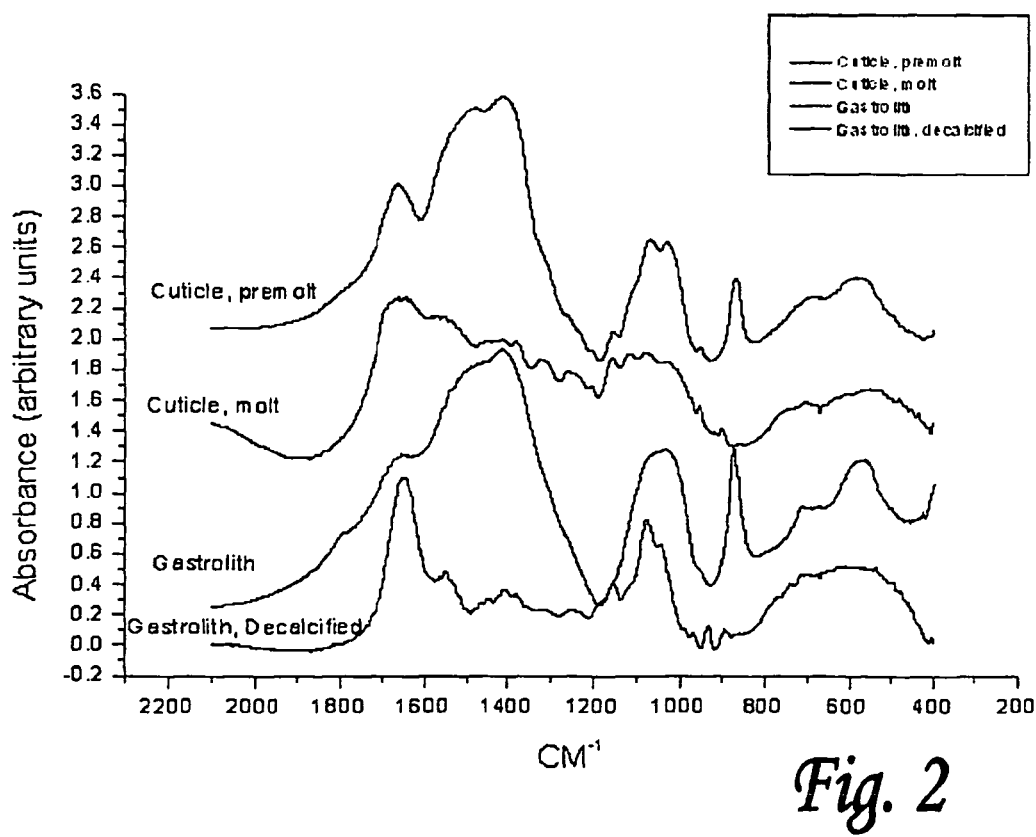
FIG. 2 presents FTIR spectra of samples of crayfish gastrolith (both mineralized and decalcified) and cuticle (molt and premolt).

FTIR analysis was performed using a Bruker equinox 55 instrument. The results of FTIR analyses of the cuticle and gastrolith material are shown in FIG. 2. The four lines, from uppermost to lowermost correspond with the following samples: Cuticle, premolt; Cuticle, molt; Gastrolith (mineralized); and Gastrolith (decalcified). The peaks seen in the spectra indicate that the predominant mineral species in the samples is ACC (broad absorption band centred at 1500 $cm^{-1}$ and peak at 870 $cm^{-1}$.) Most of the other peaks are due to the presence of the other extracellular matrix components such as chitin and various matrix proteins.

Figure 5:
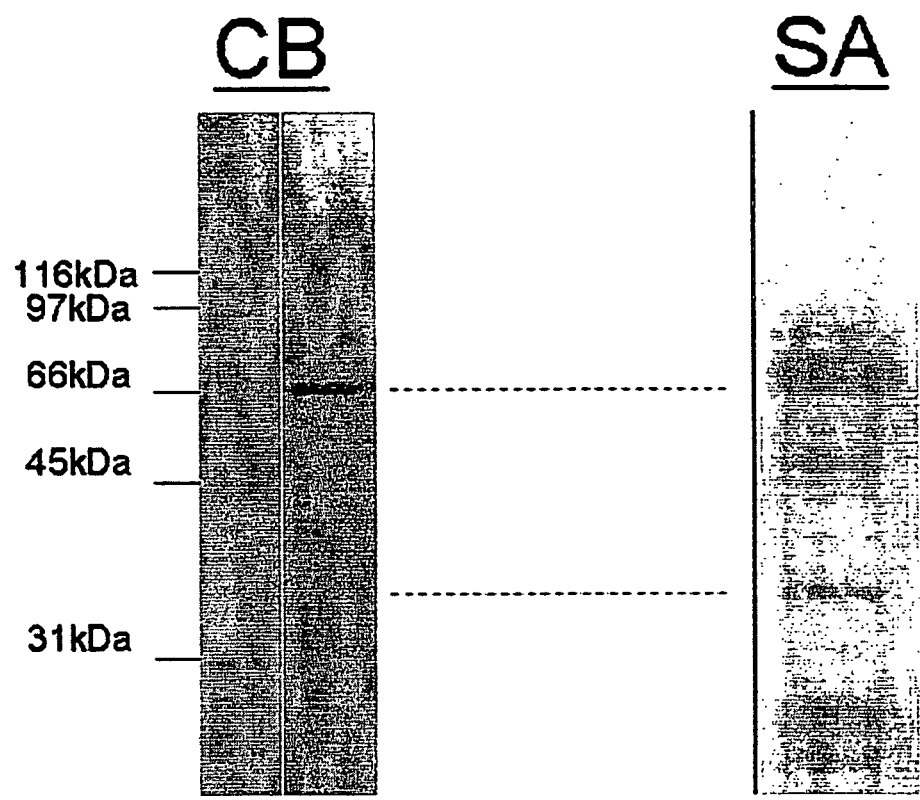
FIG. 5 is a photograph of an SDS-PAGE gel showing the protein profile of the extracellular matrix of the crayfish gastrolith. The lane shown on the left side (CB) was stained with Coomassie blue, while the lane on the right side (SA) was stained with the "Stains all" dye.

FIG. 5 shows an SDS-PAGE gel (stained with Coomassie Blue [CB] and "Stains All" [SA]) depicting a protein profile of the extracellular matrix of the crayfish gastrolith. The electrophoretic procedure was performed according to "Gel electrophoresis essential data" by D. Patel, John Wiley & Sons 1994. It may be seen that the organic matrix comprises a mixture of proteins. The most prominent bands visualized by silver staining have molecular weights of approximately 218, 184, 138, 129, 71, 66, 55, 51, 43, 30, 25 and 17 kDa.

EXAMPLE 3

Harvesting Stable ACC From Crayfish

Figure 6:
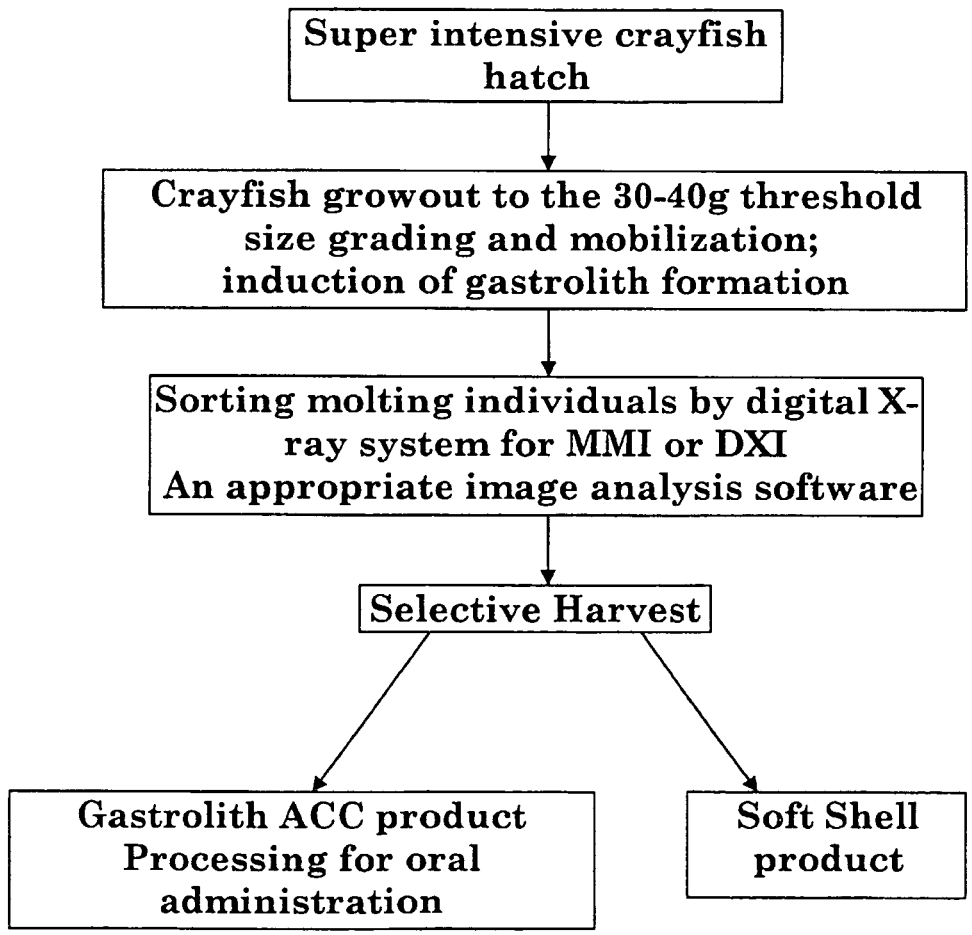
FIG. 6 schematically depicts the crayfish gastrolith harvesting method of the present invention.

Stable ACC associated with an organic matrix (in the form of gastroliths) is harvested from the gastroliths and/or the exoskeletons of crayfish by means of the scheme shown in FIG. 6.

Using the crayfish growout method developed by the inventors' laboratory [Parnes, S. & Sagi, A. (2002) Aquacult. Eng. 26: 251-262] in which a seaweed-like substrate is employed, crayfish weights of between 30 and 40 g are selected for sorting via grading devices or size adjusted traps. Under intensive conditions, the crayfish begin to reach these sizes between 50 to 70 days from the beginning of the growth period [Manor, R. et al. (2002) Aquacult. Eng. 26: 263-276]. Following size, selection, the crayfish are monitored for gastrolith development using digital X-ray imaging (DXI) (7O kV at 7 mA/0.05 sec.) and the Molting Mineralization Index (MMI, see below) developed by the inventors. In accordance with this harvest scheme, individual crayfish reaching the 30-40 g threshold will be sorted by X-ray imaging in order to select animals having an MMI of greater than 0.1, this value being indicative of animals approaching the molt event. Since this method selects for the highest capacity of natural ACC production in molting crayfish, it simultaneously enables the highest yield of natural gastroliths and of soft shell products.

Figure 3:
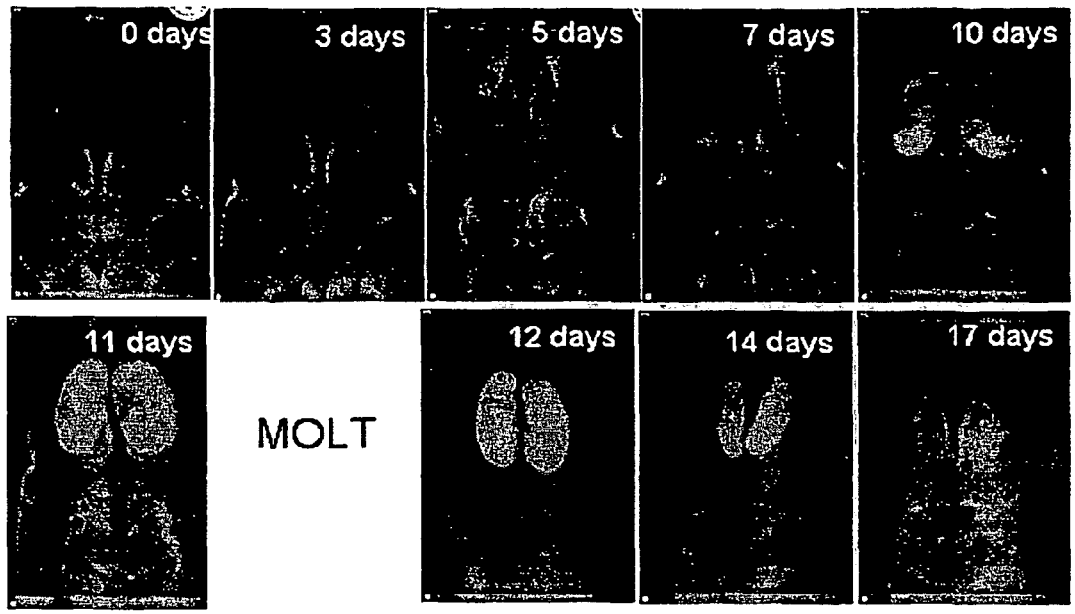
FIG. 3 is a digital X-ray image depicting crayfish gastrolith size at different molt stages.

FIG. 3 shows X-ray images of crayfish at different molt stages, the developing gastrolith being indicated by arrows. Days 0-11 represent the premolt stages and growth of the gastrolith. Ecdysis occurs between day 11 and day 12. Days 12-17 represent the postmolt stage and the degradation of the gastrolith.

Calculation of the Molting Mineralization Index (MMI):

The MMI, which has been developed in the inventors' laboratory, is based on visualization of the gastrolith using a dental X-Ray unit (Instrumentariun Imaging, mode: Focus DC) and evaluation by use of a digital X-Ray sensor (Schick Technologies). Gastrolith width is calculated by means of a calibrated metal grid (62 mm) which is placed over the image frame. Length calibration is performed using the CDR software (Schick Technologies). Carapace length is measured using a caliper and the MMI is then calculated as the ratio between gastrolith width and carapace length.

Figure 4:
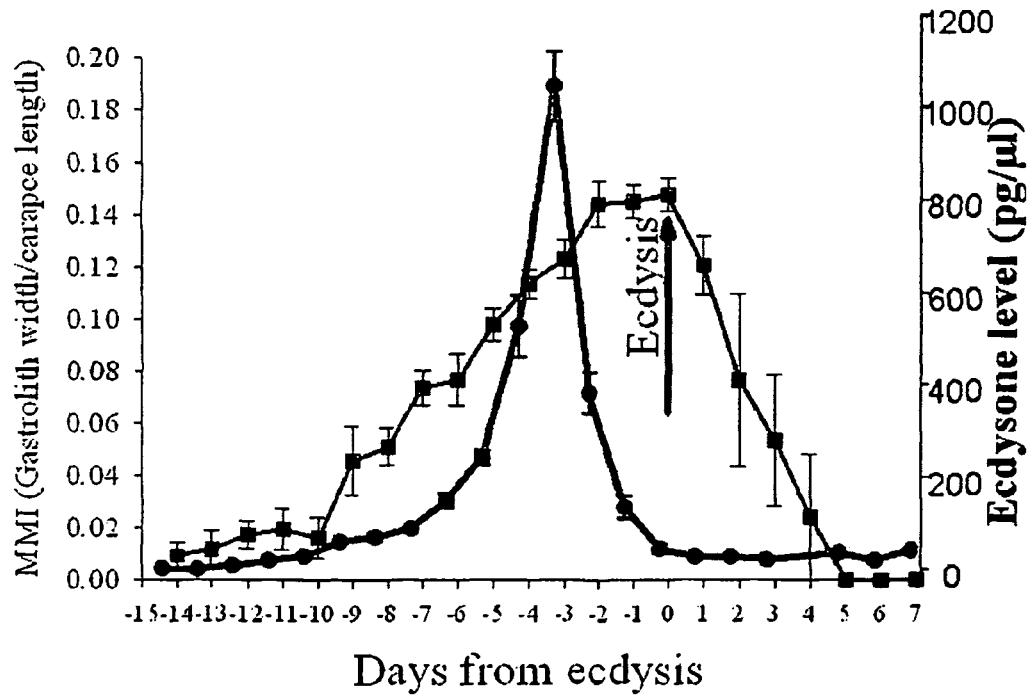
FIG. 4 graphically compares Mineralization Molt Index (MMI) and Ecdysone blood concentrations as a means of validating the use of MMI in determining the optimal point in the molt cycle for harvesting gastroliths.

The physiological precision of this method was determined by means of the following procedure: circulating 20-hydroxyecdysone (the molting hormone) in the hemolymph was measured by withdrawal of 100 μl hemolymph from the third segment of the tail following ethanol cleansing. Bleeding was carried out using a 0.65×32 mm needle, and the blood was collected in a tube containing 300 μl methanol. Radioimmunoassay (RIA) was performed in order to evaluate ecdysone levels. The results of this hormonal determination and the correlation with the MMI throughout the molt cycle are graphically illustrated in FIG. 4. In this figure, the calculated MMI values are represented by the closed square data points, while the circulating 20-hydroxyecdysone levels are represented by the closed circles.

Computerized Method for Automatic Decision-making Regarding Gastrolith Harvesting Based on DXI:

While the decision regarding the gastrolith harvesting time may be taken as described above (i.e. by manually deriving the MMI), an alternative approach is to use a computer program developed by the inventors. This program is able to perform digital X-ray image processing of the growing gastrolith and to automatically decide when molt will occur. In its present form, the software package is built to run under a Matlab work environment.

Figure 7:
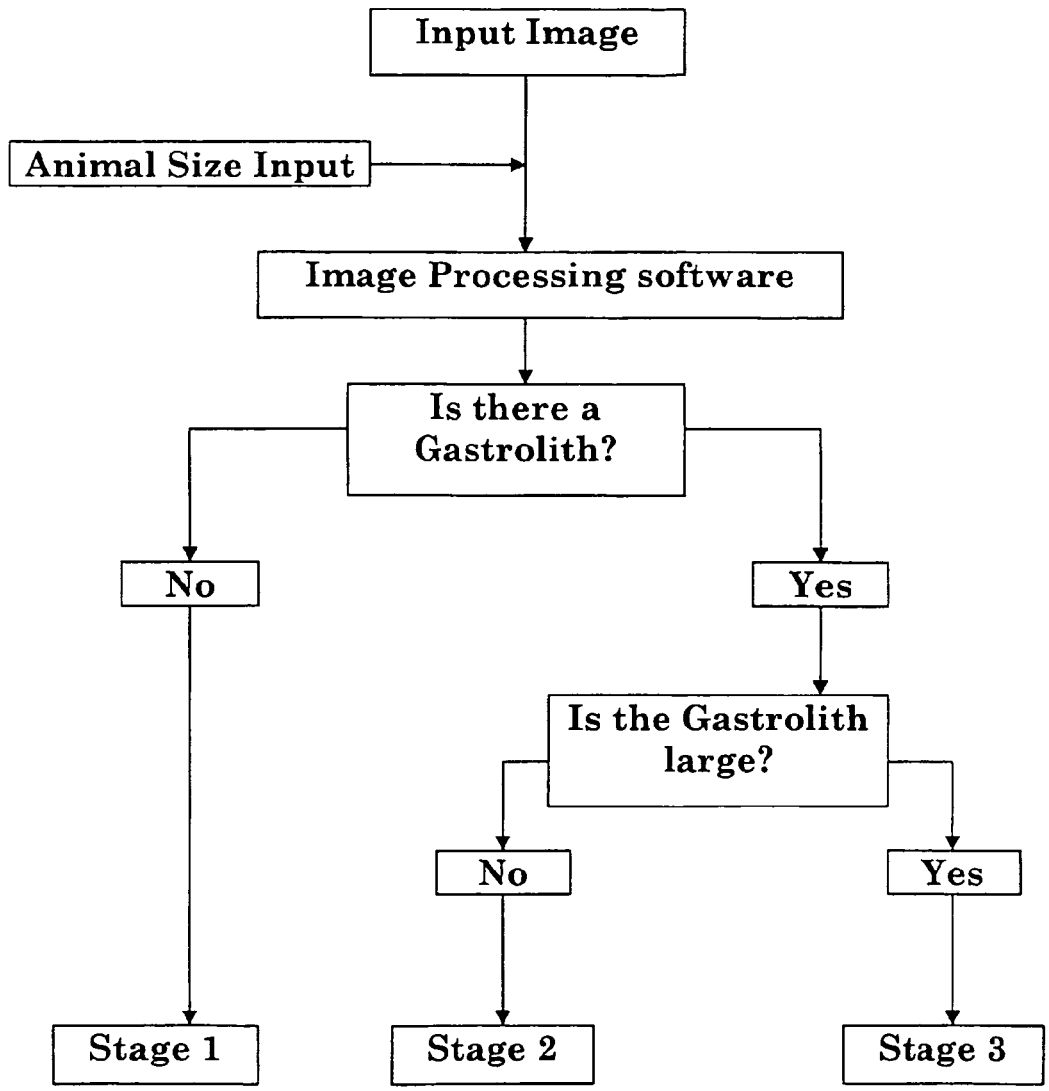
FIG. 7 schematically illustrates the various stages of the presently-disclosed method for automatic decision-making regarding gastrolith harvesting based on digital X-ray imaging (DXI).

As indicated in FIG. 7, the program requires the input of two user parameters: a digital x-ray image name, and a measure of animal size (e.g. carapace length in mm. or animal weight). First the program analyzes the digital image, using mathematical analysis based on intensity integration and power contrast modification. Then it decides, using varying mathematical techniques based on normalizing, non-linear function, whether the gastrolith is small or non-present, medium sized, or large.

Before attempting to calculate the gastrolith size, and building a mathematical model stipulating when the molt will occur, a model of what a gastrolith "looks" like was needed. Image intensity integration provided the needed solution. In this process, high intensity regions, regions of higher adsorption (white) are integrated into a single value, while lower intensity regions, regions of lower adsorption (gray-black), are considered background and discarded. The present mathematical model incorporated into the software package is able to clearly identify the gastrolith development stages.

Following analysis of the digital image, a decision is made concerning how far into the gastrolith growth process the crayfish has progressed. For this purpose, the process has been divided into 3 stages: Stage 1, either no gastrolith or a very small and insignificant gastrolith; Stage 2, a medium sized gastrolith, with the possibility for a further 2-7 days' growth; and Stage 3, wherein the gastrolith has or has almost reached its maximum size and there is, at most, 3 days remaining until molt. In order to achieve maximum accuracy, differing mathematical techniques based on non-linear functions that normalized the raw data, were used to increase the integrated intensity differences between the differing stages, while decreasing the integrated intensity differences in the stages themselves. Using this method it became possible to differentiate between stage 1 and stage 2 or 3. After which, if needed, stage 2 or stage 3 were determined.

EXAMPLE 4

Preparation of Tablets Comprising Stable ACC as the Active Ingredient—Tablet Formulation No. 1

Gastroliths are identified by the x-ray imaging technique described hereinabove in Example 3. When the gastroliths reach their maximal size, near molting time, the animals are dissected and the gastroliths harvested. The gastroliths are then washed in water, air-dried and stored in a refrigerator until further use.

The stored gastroliths are ground and then sieved. 50-100 mesh or 100-500 mesh granules are then weighed and tablets containing either 1 g or 1.5 g granules are then formed using a Carver laboratory tablet press (Model C, Fred S. Carver Inc) operating at 3 metric tons or 4 metric tons pressure without excipients.

EXAMPLE 5

Preparation of Tablets Comprising Stable ACC as the Active Ingredient—Tablet Formulation No. 2

Tablets are prepared as described in Example 4, but with the addition of either carboxymethyl starch or carboxymethyl cellulose as a disintegrant. 1.0 g of ground ACC (100-500 mesh) is mixed with the chosen disintegrant at a final concentration of 4 to 6% weight percent and subsequently compressed as described hereinabove in Example 4. Upon submerging the disintegrant-containing tablets in double distilled water, said tablets disintegrated rapidly.

EXAMPLE 6

Preparation of Capsules Comprising Stable ACC as the Active Ingredient

Capsules are prepared by manual capsule preparation using empty hard gelatin capsules or algal derived cellulose capsules from CAPSUGEL Quality®. 0.6 g of ground gastrolith powder of 100-500 mesh or 0.65 g 50-100 mesh grain size are encapsulated in each capsule.

EXAMPLE 7

Preparation of Stable ACC for Use as a Food Supplement

The gastroliths are washed in water, air-dried and ground and then sieved. >500 mesh granules are added to natural yogurt and/or other consumable food product with similar or higher viscosity for human consumption.

EXAMPLE 8

Four patients suffering from osteoporosis, age 55-78 years were daily administered tablets of gastrolith powder. One patient was receiving a daily dose of 0.5 g during four months with no changes in her situation. Other patient, receiving 1.5 g daily for 5 weeks, showed increase in bone density (the results were compared to the situation 4 years ago before osteoporosis). One patient (72 years old) was receiving 0.8 g daily for 2 months, and 1.5 g daily for 2 months. The bone density measured in the spine increased substantially (up to 13% in several regions of the bone).

EXAMPLE 9

Three patients, afflicted with several types of bone fractures comprising pelvis, back and foot (male age 40), leg (male age 9), finger (female age 40), respectively, were administered tablets of gastrolith powder for up to two weeks. The finger broken in two regions was treated for a week to a full healing. Pelvis, back and foot fractures in one wounded patient took six weeks to full recovery when taking 1.5 g daily for two weeks from the second week, whereas the initial estimation by the doctors of the recovery time was up to about six months. The patient with a broken leg took 0.5 g of gastrolith powder daily and experienced pain reduction within three days, and full recovery after a week (estimated by the doctors to take three weeks).

While specific embodiments of the invention have been described for the purpose of illustration, it will be understood that the invention may be carried out in practice by skilled persons with many modifications, variations and adaptations, without departing from its spirit or exceeding the scope of the claims.

The invention claimed is:

1. An orally-administrable composition consisting of:
   a. crayfish crustacean gastrolith derived calcified material, comprising stable amorphous calcium carbonate (ACC) present in association with an organic matrix consisting of chitin and proteins, and
   b. one or more excipients selected from the group consisting of diluents, binders, fillers, lubricants, glidants, disintegrants, emulsifying agents, flavoring agents, sweeteners and buffers;
   wherein said composition is formulated for oral administration in a dosage form selected from the group consisting of tablets, capsules, lozenges, pastilles, a liquid suspension and gel.

2. The orally-administrable composition according to claim 1, wherein the stable ACC is characterized by FTIR analysis as having a broad absorption band centred at 1500 cm$^{-1}$ and a peak at 870 cm$^{-1}$, indicative of ACC, and a peak at 1650 cm$^{-1}$, indicative of chitin.

3. The orally-administrable composition according to claim 1, wherein the stable ACC is characterized by having an FTIR spectrum as shown in FIG. 2.

4. An orally-administrable composition according to claim 1, wherein the stable ACC is characterized by an X-ray diffraction pattern displaying broad peaks centered at approximately 2θ=30° and at approximately 2θ=45°, indicative of ACC and a peak at approximately 2θ=19°, indicative of chitin, said pattern being essentially free of a signal indicative of crystalline calcium carbonate.

5. The orally-administrable composition according to claim 4, wherein the stable ACC is characterized by having an X-ray diffraction spectrum as shown in FIG. 1.

6. The orally-administrable composition according to claim 1, wherein the proteins have molecular weights of approximately 218, 184, 138, 129, 71, 66, 55, 51, 43, 30, 25 and 17 kDa, as determined by SDS-PAGE analysis.

7. An orally-administrable composition according to claim 6, wherein the stable ACC is characterized by having an SDS-PAGE electrophoretic profile similar to that shown in FIG. 5.

8. The orally-administrable composition according to claim 1, wherein the crayfish crustacean is *Cherax quadricarinatus*.

9. A process for preparing an orally-administrable composition according to claim 1, wherein said process comprises the steps of harvesting gastroliths from crayfish, grinding said gastroliths to form a powder, and formulating said powder into an orally-administered dosage form in a dosage form selected from the group consisting of tablets, capsules, lozenges, pastilles, a liquid suspension and gel.

10. A method for supplementing oral calcium intake in a subject, wherein said method comprises oral administration of a composition according to claim 1.

11. A method for treating a bone fracture or a disease selected from the group consisting of osteoporosis, osteomalacia, and hypocalcemia, wherein said method comprises oral administration of a therapeutically-effective amount of a composition according to claim 1.

12. An orally-administrable composition comprising crayfish crustacean gastrolith derived calcified material, comprising stable amorphous calcium carbonate (ACC) present in association with an organic matrix consisting of chitin and proteins, said composition further comprising one or more excipients selected from the group consisting of diluents, binders, fillers, lubricants, glidants, disintegrants, emulsifying agents, flavoring agents, sweeteners and buffers; wherein said composition is formulated for oral administration in a dosage form selected from the group consisting of tablets, capsules, lozenges, pastilles, a liquid suspension and gel.

13. The orally-administrable composition according to claim 12, wherein the stable ACC is characterized by FTIR analysis as having a broad absorption band centered at 1500 cm$^{-1}$ and a peak at 870 cm$^{-1}$, indicative of ACC, and a peak at 1650 cm$^{-1}$ indicative of chitin.

14. The orally-administrable composition according to claim 12, wherein the stable ACC is characterized by having an FTIR spectrum as shown in FIG. 2.

15. The orally-administrable composition according to claim 12, wherein the stable ACC is characterized by an X-ray diffraction pattern displaying broad peaks centered at approximately 2θ=30° and at approximately 2θ=45°, indicative of ACC and a peak at approximately 2θ=19°, indicative of chitin, said pattern being essentially free of a signal indicative of crystalline calcium carbonate.

16. The orally-administrable composition according to claim 15, wherein the stable ACC is characterized by having an X-ray diffraction spectrum as shown in FIG. 1.

17. The orally-administrable composition according to claim 12, wherein the proteins have molecular weights of approximately 218, 184, 138, 129, 71, 66, 55, 51, 43, 30, 25 and 17 kDa, as determined by SDS-PAGE analysis.

18. The orally-administrable composition according to claim 17, wherein the stable ACC is characterized by having an SDS-PAGE electrophoretic profile similar to that shown in FIG. 5.

19. The orally-administrable composition according to claim 12, wherein the crayfish crustacean is *Cherax quadricarinatus*.

20. An orally-administrable composition consisting of:
   a. crayfish crustacean gastrolith derived calcified material, comprising stable amorphous calcium carbonate (ACC) present in association with an organic matrix consisting of chitin and proteins, and
   b. one or more excipients, selected from the group consisting of diluents, binders, fillers, lubricants, glidants, disintegrants, emulsifying agents, flavoring agents, sweeteners and buffers, wherein said composition is formulated for oral administration in a powder or granulated dosage form, having a 50-100 mesh grain size.

* * * * *